(12) United States Patent
Koenig

(10) Patent No.: US 6,588,690 B1
(45) Date of Patent: Jul. 8, 2003

(54) SYSTEM AND METHOD FOR TREATING PROCESS MATERIAL

(75) Inventor: Larry E. Koenig, Pickerington, OH (US)

(73) Assignee: Komar Industries, Inc., Groveport, OH (US)

(*) Notice: Subject to any disclaimer, the term of this patent is extended or adjusted under 35 U.S.C. 154(b) by 0 days.

(21) Appl. No.: 09/525,621

(22) Filed: Mar. 14, 2000

(51) Int. Cl.[7] ............................................. B02C 19/22
(52) U.S. Cl. .................... 241/65; 241/260.1; 241/606
(58) Field of Search ........................ 241/23, 65, 260.1, 241/299, 606; 414/218

(56) References Cited

U.S. PATENT DOCUMENTS

| | | | |
|---|---|---|---|
| 2,708,074 A | 5/1955 | Hoskins | |
| 2,731,208 A | 1/1956 | Dodd | |
| 3,841,465 A | * 10/1974 | Miller et al. | 241/247 |
| 4,578,185 A | 3/1986 | Wilson et al. | |
| 4,670,227 A | 6/1987 | Smith | |
| 4,881,862 A | * 11/1989 | Dick | 414/218 |
| 4,884,756 A | 12/1989 | Pearson | |
| 4,915,308 A | * 4/1990 | Koenig | 241/260.1 |
| 4,974,781 A | 12/1990 | Placzek | |
| 5,048,766 A | 9/1991 | Gaylor et al. | |
| 5,054,696 A | * 10/1991 | Mennel et al. | 241/260.1 |
| 5,087,420 A | 2/1992 | Jackson | |
| 5,089,228 A | 2/1992 | Meijer | |
| 5,116,574 A | 5/1992 | Pearson | |
| 5,119,994 A | 6/1992 | Placzek | |
| 5,167,372 A | 12/1992 | Poggie et al. | |
| 5,190,226 A | 3/1993 | Holloway | 241/23 |
| 5,277,136 A | 1/1994 | Davis | |
| 5,346,142 A | 9/1994 | Miller et al. | |
| 5,360,594 A | 11/1994 | Meijer | |
| 5,362,443 A | 11/1994 | Tanaka et al. | |
| 5,364,589 A | 11/1994 | Buehler et al. | |
| 5,384,092 A | 1/1995 | Sawhill et al. | |
| 5,389,347 A | 2/1995 | Hall | |
| 5,427,737 A | 6/1995 | Glazer et al. | |
| 5,470,022 A | 11/1995 | Wright et al. | |
| 5,566,890 A | 10/1996 | Ricciardelli | |
| 5,570,845 A | 11/1996 | Lewis et al. | |
| 5,635,122 A | 6/1997 | Vezzani | |
| 5,649,785 A | 7/1997 | Djerf et al. | |
| 5,941,468 A | 8/1999 | Lewis et al. | |

FOREIGN PATENT DOCUMENTS

WO  WO 93/06931  4/1993

* cited by examiner

Primary Examiner—Mark Rosenbaum
(74) Attorney, Agent, or Firm—Standley & Gilcrest LLP

(57) ABSTRACT

A method and system for treating material, especially medical waste, municipal solid waste and paper, such as newsprint. The system includes an input component having an air lock and shredder; a pressurized treatment component which includes a feed screw which feeds material into an extrusion tube that is connected to a rotating autoclave vessel, a pressurized outlet hopper, and an exit feed screw which feeds sterilized material into an outlet extrusion tube. The system also includes a drying and cooling component which receives material from the outlet extrusion tube, tumbles the material in a drum to break it up, cool it and release moisture, and an evacuation blower which conveys moist air in the drum through a condenser. In a preferred embodiment, the autoclave vessel is sealed at its inlet and outlet ends in part by dynamic plugs of material which progress through the inlet and outlet extrusion tubes, but at the same time form compacted, airtight barriers which seal the autoclave vessel.

35 Claims, 8 Drawing Sheets

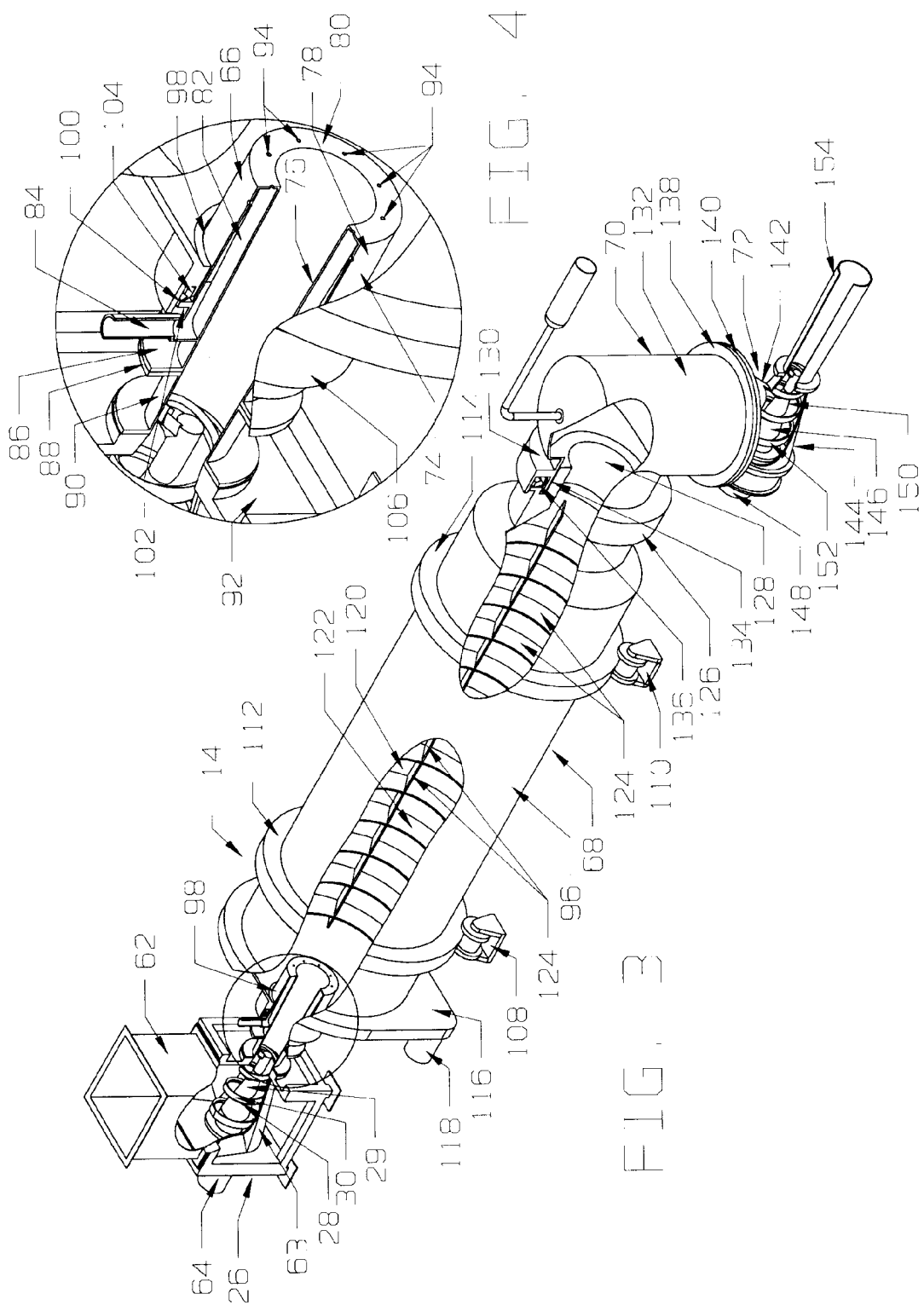

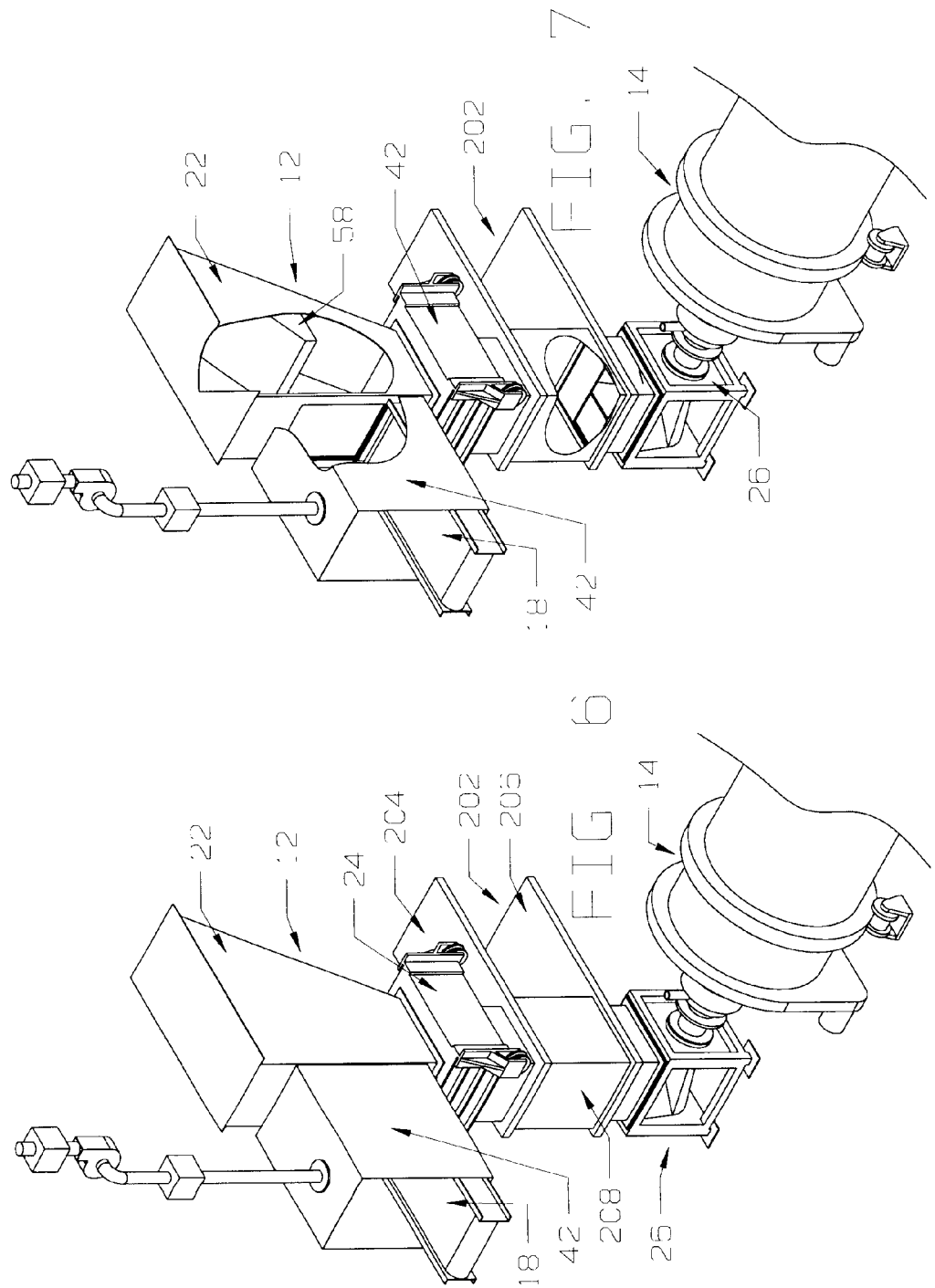

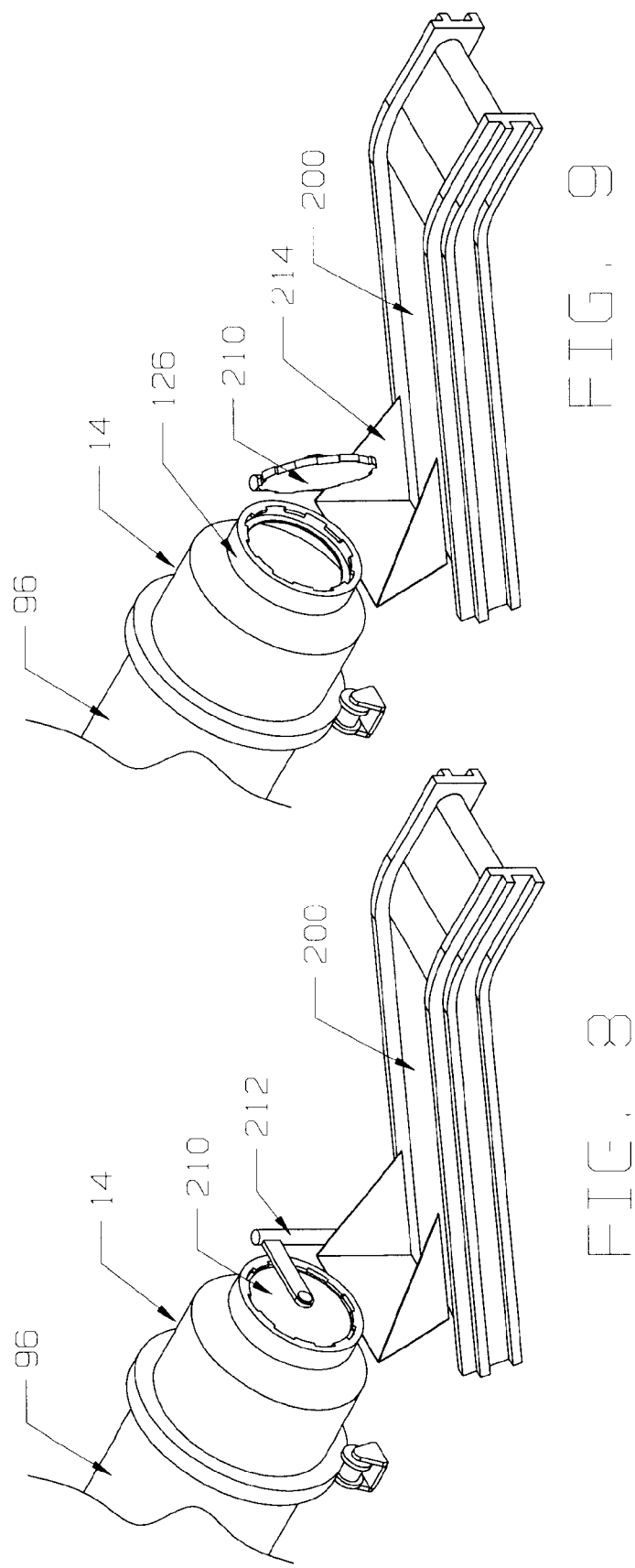

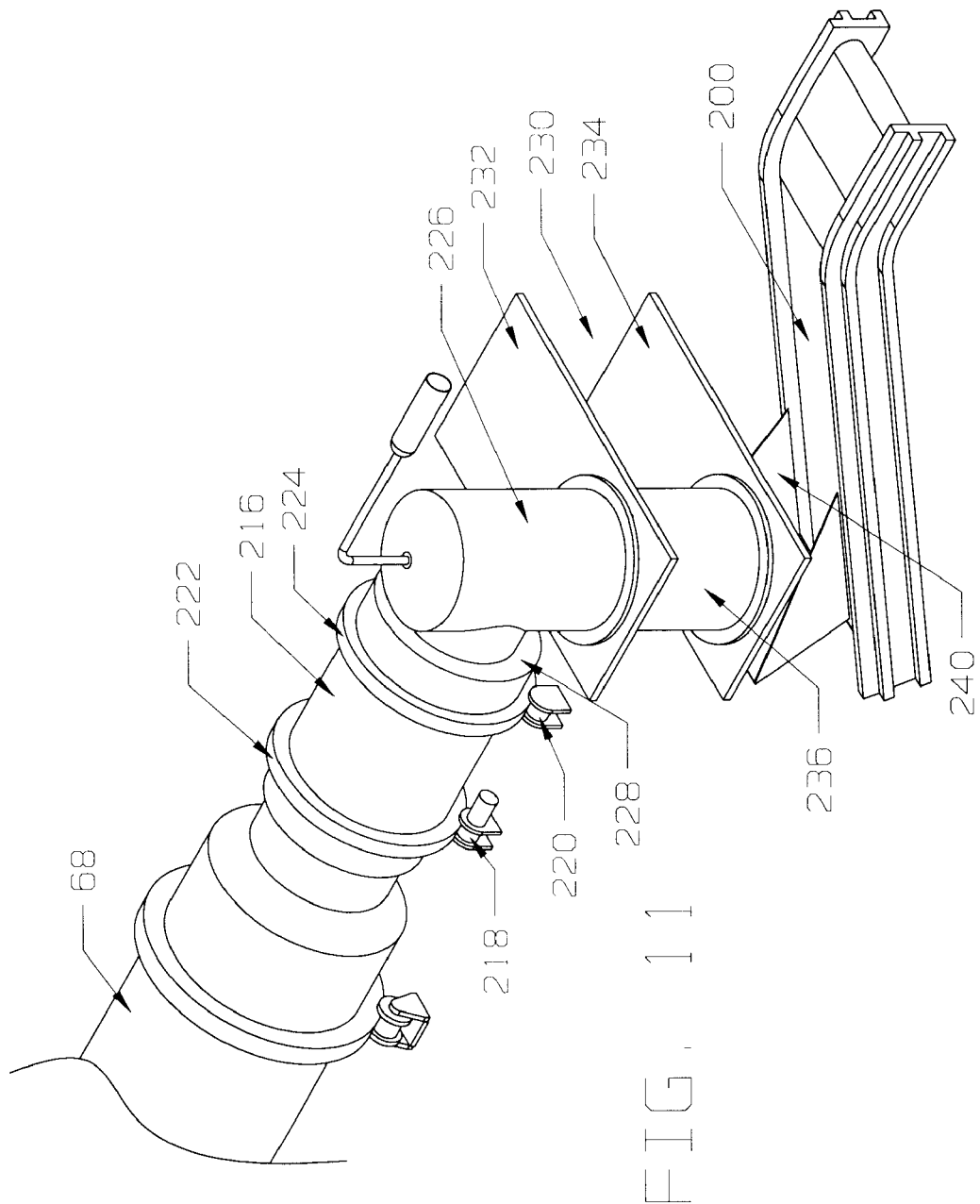

SYSTEM AND METHOD FOR TREATING PROCESS MATERIAL

BACKGROUND OF THE INVENTION

The present invention relates to systems and methods for treating process material and, more particularly, to systems and methods for treating municipal solid waste material, medical waste material, reclaimed paper and the like.

As a result of increasing scarcity of landfills and more stringent environmental regulations, efforts have been made to reduce the volume of process material, such as municipal solid waste ("MSW") and paper material, such as newsprint and other reclaimed and recycled paper products as a step in the process of disposing of the material, either by depositing it in landfills, incinerating it or recycling it. Processes have been developed to break down such material for disposal, or in the case of paper products, use as insulation. An example of such a process and device is Holloway U.S. Pat. No. 5,190,226. That patent discloses an apparatus and method for separation, recovery and recycling of MSW. The apparatus includes a rotating drum which is fed at an upstream end by a reciprocating ram, a steam source which is connected to introduce high temperature steam into the drum, and a spiral rib or flight mounted within the drum to transport material deposited in an upstream end of the drum along the length of the drum.

The drum is maintained in a pressurized state during a sterilization process by inlet and exit air locks which are connected to and enclose the inlet and outlet of the rotating drum. The outlet air lock is connected to a rotating trommel which receives sterilized waste from the drum and rotates it over screens to provide a sizing function.

In view of heightened concerns over the spread of infectious diseases, many of which are fatal to humans, governmental agencies have imposed strict requirements on the disposal of waste, and more particularly, medical waste. Such medical waste may include relatively soft items such as hospital linen, garments worn by patients and health care providers, bandages, gauze and other fabric material which comes in contact with a patient, as well as harder materials such as disposable plastic surgical instruments and hypodermic needles. In order to treat such materials to render them safe and at the same time comply with federal, state and local standards, it is often necessary to grind, shred, or otherwise comminute such medical waste, and in addition, to sterilize the waste by heating it, contacting it with a disinfectant, or a combination of both. Furthermore, as in most sterilization processes, it is necessary that the actual sterilization steps be conducted in a closed and controlled atmosphere.

An example of such a device and method is shown in Lewis et al. U.S. Pat. No. 5,941,468. That patent discloses a medical waste sterilization system in which medical waste is shredded and placed in a rotating autoclave cylinder where it is first tumbled and contacted by steam to heat it, then is heated further in a downstream section of the autoclave cylinder which is surrounded by a steam jacket. The waste is then cooled and dehydrated in a third section of the cylinder and deposited in a compactor. The object of the device and method is to heat the medical waste thoroughly to a sterilizing temperature (typically above 212° F. for at least 30 minutes), then dehydrate the material to reduce its volume and weight.

A disadvantage with such systems is that, while they may be effective in treating MSW or process material, or sterilizing medical waste, they either operate on a batch process, that is, as in the device of aforementioned U.S. Pat. No. 5,190,226 the heating vessel is first loaded with solid waste, rotated to expose the waste to steam at elevated temperature and pressure, then the waste is evacuated from the rotating drum or pressure vessel completely before new waste is introduced for sterilization; or, as in the device of U.S. Pat. No. 5,941,468, the vessel is maintained below ambient pressure since no air-tight seal is effected in the waste material inlet and outlet openings of the vessel.

A second disadvantage with such systems is that the heating of material is performed entirely within a rotating drum or other vessel which typically has a volume—much larger than that of the waste material to be sterilized. As a result, the entire interior volume of the drum must be heated to the desired temperature, and the waste tumbled to expose it to steam so that it is heated evenly. Consequently, a larger amount of steam, and therefore heat energy, is required to heat the entire interior of the vessel, in comparison to the amount of steam and heat energy to required to heat simply the waste material itself.

Accordingly, there is a need for a material treatment system and method which can utilize a pressurized vessel operated on a continuous basis, as opposed to being operated on a batch basis, the latter process having the disadvantage of providing a reduced throughput rate, and further, requires successive heating and cooling cycles which require relatively large amounts of energy. There is also a need for a system and method for treating material, including medical waste, in which the energy needed to heat the material is concentrated on the material itself, as opposed to a process in which material is heated simply by placing it in a large volume, the entirety of which must be heated to the necessary temperature.

SUMMARY OF THE INVENTION

The present invention is a system and method for treating material under pressure in which the material is compacted into a plug within an inlet extrusion tube and preheated, then heated to the desired temperature within a rotating autoclave vessel fed by the extrusion tube. In a preferred embodiment of the present invention, the system includes inlet and outlet extrusion tubes through which material to be treated enters and exits a pressurized treatment zone which includes the autoclave vessel. Inlet and outlet injector screws feed material into the inlet and outlet extrusion tubes, respectively, to create continuously moving or "dynamic," air-tight plugs of material within the tubes to seal the treatment zone.

Since it is the material itself that forms the seals of the pressurized treatment zone inlet and outlet, the system of the present invention can perform a treating function on a continuous basis, even though the vessel is pressurized above ambient. This design represents an improvement over prior art devices in which material treatment is performed in autoclaves which are sealed with a conventional gate or door, such that the treatment process must be performed in a batch mode. As a result, the system and process of the present invention provides a greater throughput rate than prior art designs and processes, and a concomitant greater energy efficiency, since the pressurized treatment zone does not need to be successively heated to treat material, then cooled to allow the material to be removed at a safe handling temperature.

The system and method of the present invention is effective in treating medical waste, in which case the material is heated and retained within the pressurized treatment zone sufficiently to sterilize it, preferably being heated to at least 212° F., as well as MSW and paper, such as newsprint, in which case the material is heated and retained within the pressurized treatment zone sufficiently to "cook" it and break it down, especially the paper fibers. Medical waste, MSW and paper shall be referred to herein collectively as "material."

In a preferred embodiment of the invention, the system has an input component which includes a conveyor which conveys material through an air lock to a hopper, a shear shredder which receives material from the hopper and shreds it to reduce its size, and an injector screw which receives the shredded material and feeds it to the inlet extrusion tube of the pressurized treatment zone. In alternate embodiments, the input component includes a hopper having a reciprocating ram which forces material into the shear shredder, and an air lock, located between the shear shredder and the injector screw, which eliminates the need for an air lock associated with the conveyor.

The central component of the present invention is the pressurized treatment zone, which includes a rotating autoclave vessel. Essential to the operation of the rotating autoclave vessel is the heated inlet extrusion tube which connects the inlet feed screw with the interior of the autoclave vessel. The inlet extrusion tube preferably comprises a cylindrical tube having a slightly diverging interior wall, a chamber for receiving pressurized, heated steam, and an inner face with orifices shaped and oriented to direct steam from the interior of the extrusion tube into the interior of the autoclave. It is within this extrusion tube that material received by the inlet injector screw and compacted to form an air-tight plug, heated and largely sterilized (if desired) prior to its entering the autoclave vessel. Since the material is compacted and in intimate contact with the heated extrusion tube, the heating is more efficient than in prior art vessels which are largely empty during operation.

The autoclave vessel is a horizontally-oriented cylinder which is mounted for rotation. The interior of the vessel includes a continuous, helical rib so that rotation of the vessel about its central, longitudinal axis causes material deposited within it to progress along the length of the vessel. The interior of the vessel is heated exclusively by the steam which exits the orifices formed in the extrusion tube. The purpose of the vessel is to fluff the material and expose it thoroughly to the heat from the steam, which will sterilize medical waste and cook and break down MSW and paper pulp. The helical rib located within the vessel includes a plurality of longitudinally-extending ribs which extend between flights and act to lift the hazardous material and tumble it as it progresses along the vessel. This further ensures the even heating and sterilization of the material.

In the preferred embodiment, the vessel includes an open exit end which empties into a stationary, vertically-oriented pressure vessel or hopper. That pressurized hopper directs the now-treated material downwardly into a second or exit injector screw which feeds it into a second or exit extrusion tube, forming a plug of material. This downstream or exit plug of material also acts as a seal so that the atmosphere within the pressure vessel, pressurized hopper, and exit injector screw is sealed from the environment. The exit extrusion tube preferably is connected to, and therefore deposits treated material into, a tumbler, where the material is dehydrated and cooks. The tumbler preferably includes an exhaust blower which maintains the interior of the tumbler at a slightly-below-atmospheric pressure. The tumbler also includes a helical rib which causes the material to break apart as it progresses along the tumbler, and the tumbler is open at its exit end so that the material may be deposited upon a conveyor for removal.

In an alternate embodiment, the exit injector screw and exit extrusion tube are replaced by an air lock which acts to seal the interior of the vessel and stationary exit vessel from the ambient. Also in alternate embodiments, the exit air lock is replaced with a sealable door so that the sterilization process may be conducted, if desired, on a batch basis. With that embodiment, the pressure vessel processes material along its length, then after the material has been adequately heated, the exit door is opened and the treated material is forced outwardly through it by the helical ribs within the vessel unto a conveyor for removal. However, the inlet injector screw and inlet extrusion tube of that embodiment allow continuous feeding into the pressurized autoclave vessel during treatment.

With all of the embodiments summarized above, the input component, which includes an injector screw, creates a plug within an inlet extrusion tube which acts as a dynamic seal, since the material progressing through the extrusion tube into the vessel seals the interior of the autoclave vessel from the ambient and from the shredding and input segments of that component.

The method of the present invention includes the steps of receiving material within an enclosed environment, shredding the material within that environment, forming a dynamic plug of shredded material while simultaneously heating the material to a predetermined temperature (preferably greater than 212° F.), depositing the heated material into a rotating vessel where it is broken up and maintained at a temperature above 212° F., then cooling and dehydrating the material. Also in the preferred method, the treated material is formed into a dynamic plug which seals the pressurized treatment zone of the apparatus.

Accordingly, it is an object of the present invention to provide a system and apparatus for treating material in which the material can be heated under pressure on a continuous basis if desired; a system and method for treating waste in which the waste itself is formed into dynamic plugs which form seals to isolate the heating regions of the apparatus from the input and exit regions; and a system and method for heating material which is rugged and can be modified easily to perform treatment of material on a batch basis, if desired.

Other objects and advantages of the present invention will be apparent from the following description, the accompanying drawings and the appended claims.

BRIEF DESCRIPTION OF THE DRAWINGS

FIG. 3 is a schematic, perspective view of the detail of FIG. 2, partially broken away to reveal the inlet and outlet injector screws, input and exit extrusion tubes and sterilization vessel;

FIG. 4 is a detail showing a schematic, perspective view of the inlet extrusion tube of the device of FIG. 3;

FIG. 6 is a schematic, perspective view of an alternate embodiment of the input component of the preferred embodiment of the present invention;

FIG. 7 is a schematic, perspective view of the input component of FIG. 6, partially broken away to reveal the interior of the air locks and feed hopper;

FIG. 8 is a schematic perspective view of an alternate embodiment of the invention in which the pressure vessel is sealed with a door;

FIG. 9 is embodiment of FIG. 8 showing the door in an open position;

FIG. 11 is a detail of an alternate embodiment of the present invention showing an air lock at the exit end of the vessel.

DETAILED DESCRIPTION

Figure 1:
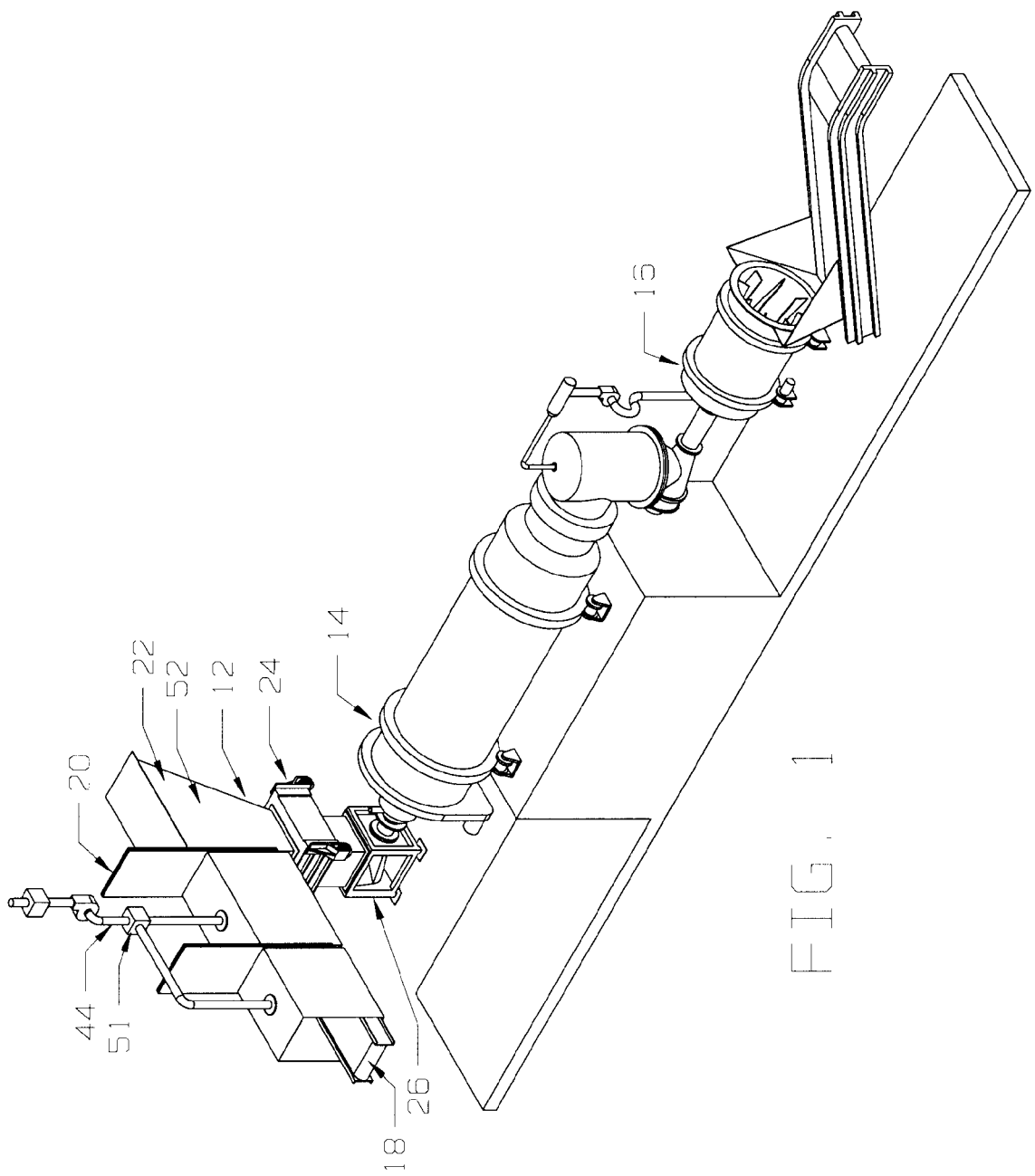
FIG. 1 is a somewhat schematic, perspective view of a system embodying a preferred embodiment of the system and method of the present invention.

As shown in FIG. 1, the system of the present invention includes an input or feeding component 12, a pressurized treatment component 14, and a cooling and drying or output component 16. The input component 12 includes an input conveyor system 18, an air lock 20, an input hopper 22, a shredder 24 and a feed or compression screw 26.

Figure 5:
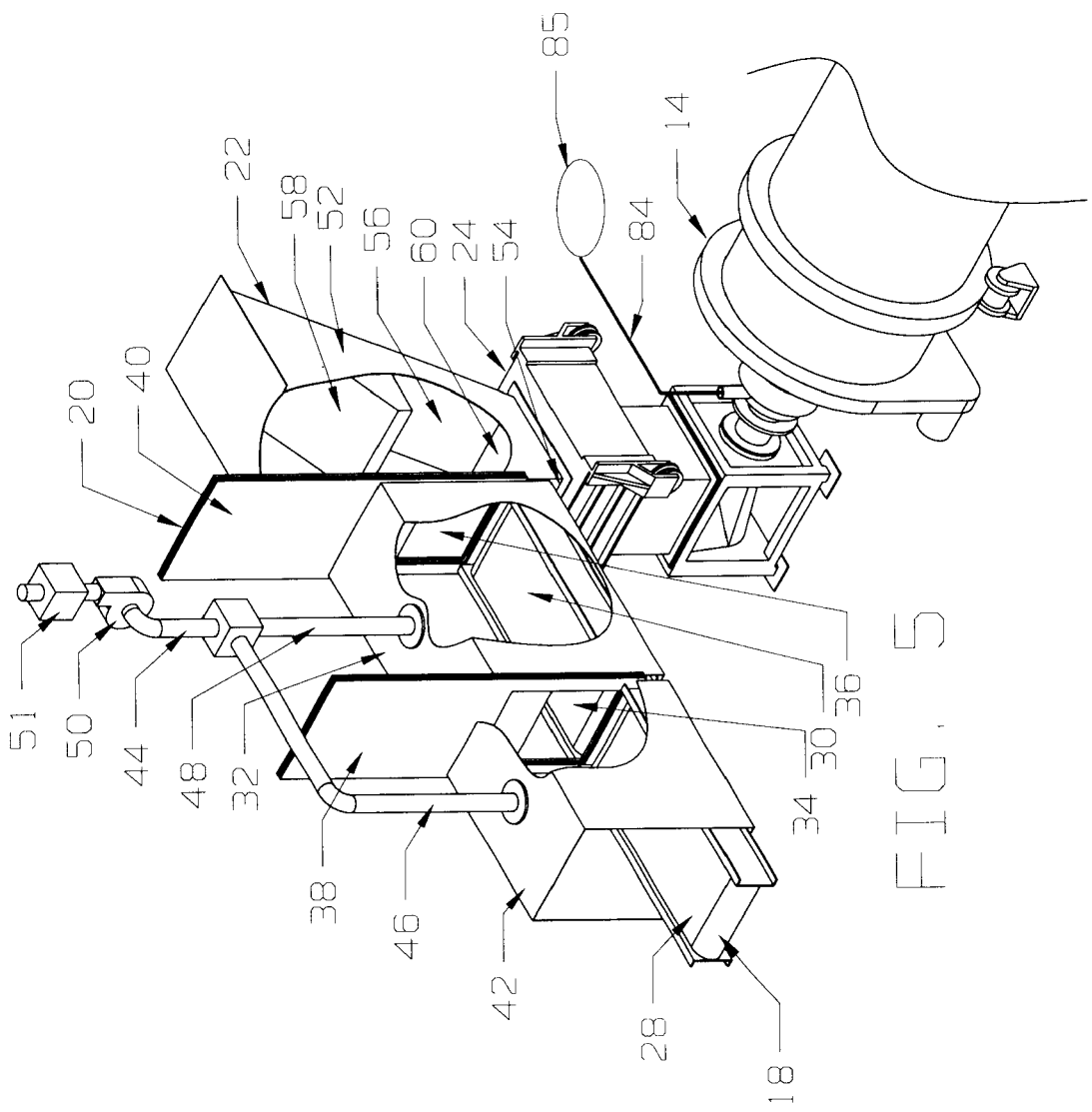
FIG. 5 is a schematic, perspective view of the input component of the system of FIG. 1.

The conveyor system 18 includes an input conveyor 28 and, as best shown in FIG. 5, an air lock conveyor 30 which is aligned with the input conveyor 28. The air lock 20 includes an enclosure 32 having an input opening 34 and an outlet opening 36, which are alternately opened and closed by inlet and outlet gates 38, 40, respectively. The input conveyor 28 is enclosed on four sides by a hood 42. An exhaust system, generally designated 44, includes conduit 46, which communicates with the hood 42, and conduit 48, which communicates with the air lock enclosure 32. The exhaust system 44 includes a blower 50 and a HEPA (high efficiency particulate air) filter 51.

The feed hopper 22 includes an enclosure 52 having a front wall 54 which is common with the air lock 32 and in communication with the exit opening 36, and a converging rear wall 56. A reciprocating ram 58 is positioned within the hopper 22 and is operated by a double-acting cylinder (not shown). The hopper 22 includes a bottom opening 60 which is in communication with the shredder 24. Shredder 24 preferably is a shear shredder, such as Komar Industries, Inc. Model QR3030-50.

Figure 2:
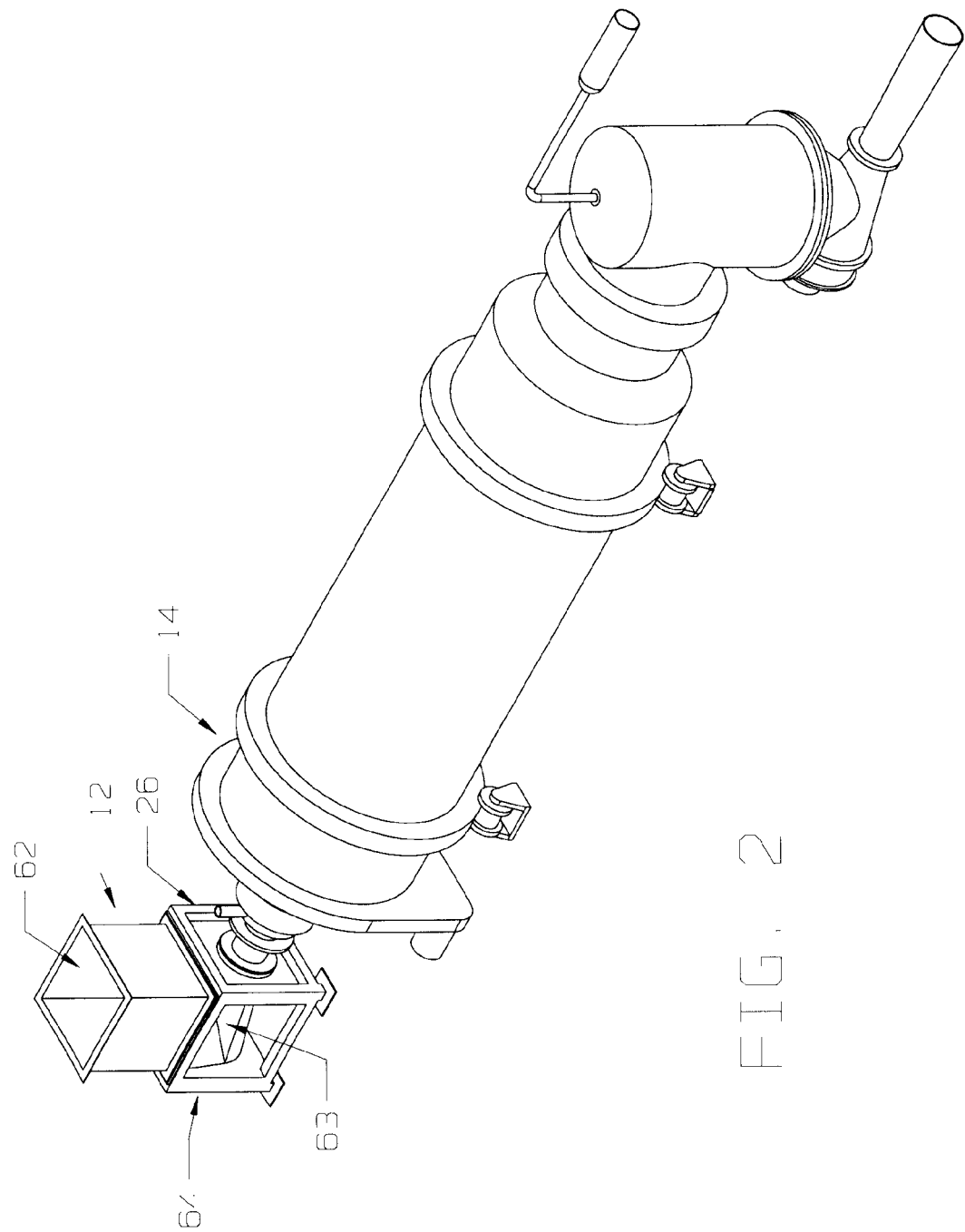
FIG. 2 is a somewhat schematic, perspective detail of the system of FIG. 1 showing the vessel, inlet injector screw and outlet injector screw.

As best shown in FIGS. 2 and 3, the feeding component 12 includes a feed screw hopper 62 which interconnects the hopper enclosure 52 (FIG. 5) with the feed screw 26. The feed screw 26 includes a screw 27 having a tapered shaft 29 and a helical flight 31 which is oriented horizontally within an enclosure 63 which conforms generally to the tapered, conical shape of the screw. The screw 27 is powered by a bidirectional, variable speed hydraulic motor 64.

The operation of the feed component 12 is as follows. As shown in FIG. 5, material (not shown), such as containerized medical waste, is placed on input conveyor 28. The atmosphere within the hood 42 is slightly below atmospheric as a result of the operation of the blower 50, so that fumes are drawn through the HEPA filter 51. The air lock door 38 is opened and the conveyor 28 conveys the containerized waste onto the air lock conveyor 30. The door 38 then closes, and subsequently, air lock outlet door 40 opens, conveyor 30 is actuated, and the material is conveyed into the feed hopper 52, where it falls downwardly into the shear shredder 24. If the material "hangs up" or bridges the rotating shredder components of shear shredder 24, the reciprocating ram 58 is cycled to force the material downwardly to be shredded by the shredder 24. The shredded material enters the feed screw enclosure 63 where it is transported horizontally and, simultaneously, compressed by the screw 28.

As shown in FIGS. 3 and 4, the pressurized treatment component 14 of the present invention includes an inlet extrusion tube, generally designated 66, a rotating autoclave vessel 68, an evacuation hopper 70, and an outlet injector screw assembly 72. The inlet extrusion tube 66 extends into the interior of the vessel 68 and includes a generally cylindrical, horizontally-extending body 74 having an inner wall 76 which tapers outwardly along its length (preferably about ½" of diameter for 3' of length), an outer, generally cylindrical wall 78, and a squared end face 80. The inner and outer walls 76, 78 form a steam jacket or chamber 82 which is generally cylindrical in shape and communicates with a steam supply conduit 84. The conduit 84 is connected to a source of steam 85 (FIG. 5). The upstream end of the tube 74 includes a flange 86 which mates with a corresponding flange 88 which is part of an extension 90 connected to the downstream wall 92 of the feed screw enclosure 63.

The face 80 is perforated with a plurality of orifices 94 which communicate with the chamber 82 so that steam entering the chamber will exit through the orifices 94 and into the vessel 68. It is within the scope of the invention to provide additional orifices (not shown) in the outer wall 78 of the inlet extrusion tube 66 located at the inner end portion (that is, the portion of the inlet extrusion tube within the interior of the vessel 68), or to provide orifices only in the outer wall of the inner end portion of the inlet extrusion tube, and/or to provide such orifices (not shown) in the inner wall 76 of the tube at that location.

The vessel 68 includes a horizontally-extending cylindrical body 96 having an inlet opening 98 at an upstream end shaped to receive the inlet extrusion tube 66 therethrough. The outer wall 78 of the extrusion tube 66 includes a radially-extending flange 100 which forms a labyrinth seal with a correspondingly-arranged annular flange 102, and an annular gasket 104, both retained with an end extension 106. Consequently, the flanges 100, 102 and gasket 104 form a rotating seal between the stationary tube 66 and rotating body 96. The body 96 is supported on bearings 108, 110 which engage annular external ribs 112, 114, respectively, which extend about the exterior surface of the body. The body 96 is rotated by a gear drive 116 which includes an electric drive motor 118, which preferably is a variable-speed, bidirectional drive motor.

As shown in FIG. 3, the interior 120 of the body 96 includes a continuous, helical, raised rib 122 which extends along the length of the interior. The flights of the rib 122 are separated by a plurality of flat spacer plates 124 which extend radially and axially relative to the body 96. The size and spacing of the rib 122 promotes the transport of hazardous material along the length of the body 96.

The downstream end of the cylinder 96 includes an outlet extension 126 which defines an outlet opening 128 and includes a radially-inwardly extending flange 130. The pressurized hopper 70 includes a cylindrical body 132 and a flange 134 which includes a radially extending flange 136 which forms a labyrinth seal with the flange 130. The labyrinth seal created by flanges 130, 136 is of similar construction to the labyrinth seal formed between the injection tube 66 and cylinder extension 106. An annular gasket (not shown) is also included in the labyrinth seal.

The pressurized hopper 70 includes a mating flange 138 which is connected to the flange 140 of the inlet hopper 142 for the exit injector screw assembly 72. The hopper 142 is of a tapered, conical shape and communicates with a conical housing 144 of the exit injector screw assembly 72. The exit injector screw assembly 72 includes a tapered screw 146 which is driven by a variable-speed, bi-directional hydraulic motor 148. The screw 146 includes a tapered shaft 150 and a helical flight 152. The tip of the screw 146 extends into an exit extrusion tube 154 which tapers outwardly in a downstream direction. Thus, during operation of the system of the present invention, a pressurized treatment zone, which includes the cylinder 96, pressurized hopper 70, inlet hopper 142 and exit injector screw assembly 72 is created between the inlet extrusion tube 66 and the outlet extrusion tube 154, both of which are sealed by air-tight, dynamic plugs of material.

Figure 10:
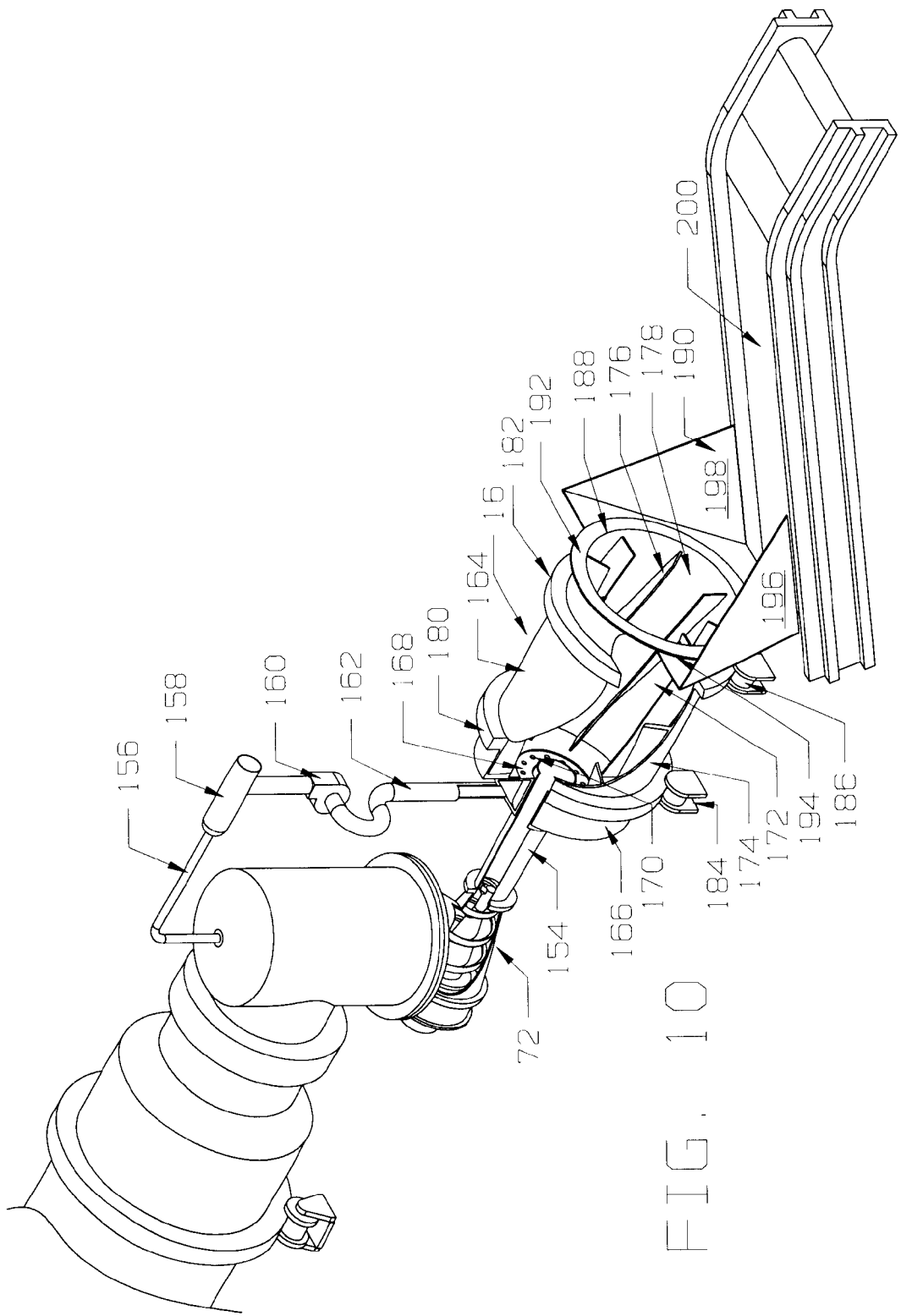
FIG. 10 is a schematic, perspective view of a detail of the system of FIG. 1 in which the outlet injector screw, exit extrusion tube and tumbler are shown broken away.

As shown in FIGS. 3 and 10, an evacuation system, generally designated 156, includes a condenser 158, blower 160 and conduit 162 which communicates with the interior of the drum 164 which is a part of the cooling and drying component 16. The conduit 162 is connected to annular chamber 166 which includes a plate 168 having a plurality of orifices 170 formed in it. The orifices 170 open into the interior 172 of the drum 164. The drum 164 includes a cylindrical body 174 having a plurality of raised ribs 176 which extend inwardly from the inner wall 178 of the drum in a spiral pattern. The drum 164 includes raised external ribs 180, 182 which engage bearings 184, 186, respectively. The drum 16 is rotated about its central longitudinal axis by a reversible electric motor (not shown). The downstream end of the drum 164 is defined by an opening 188 which communicates with an open hopper 190. The end 188 includes a radially-extending flange 192 which is received within an arcuate opening 194 of the open hopper 190. The open hopper 190 includes converging walls 196, 198 which are shaped to direct material onto a conveyor 200 for removal from the site.

The operation of the system shown in FIG. 1 is as follows. Material which has been shredded by shredder 24 and dumped into inlet feed screw enclosure 63 (see FIG. 3) is compressed and displaced sidewardly into the inlet extrusion tube 66, where friction between the material and the inner wall of the tube causes the material to form a compacted plug (not shown) within the tube. The material within the tube 66 is heated by steam which is injected into the chamber 82 through conduit 84. The steam entering the chamber preferably is between 250° F. and 280° F., but in any event is above 212° F. As additional material is driven into the tube 66 by the screw 28, material is forced from the end of the tube adjacent to the perforated face 80 and is deposited into the cylinder 96. Additional size reduction of the material is accomplished by the abrasion of tip of the shaft and tip of the flight 30 of the screw 28 against the adjacent material of the non-rotating plug within the tube 66.

The material within the inlet extrusion tube 66 is sufficiently compacted to provide an airtight plug which seals the inlet to the vessel cylinder 96. However, this airtight plug is dynamic in that it is composed of a progression of comminuted waste material which is being fed continuously into the cylinder 96 by screw 28. Consequently, as material leaves the tube 66 and is deposited within the cylinder 96, it is replaced at the upstream end of the tube by material which has fallen downwardly into the feed screw enclosure 63 and is "pumped" sidewardly by the tapered screw 28. This tapered screw 28 not only abrades the material falling within the chamber 32 against the non-rotating plug of material within the tube 66, thereby further reducing its size, the tapering shaft 29 of the screw 28, in combination with the helical flight of that screw, compresses the material into the tube 66. Consequently, the material within the tube 66 is heated to the desired temperature by steam in the steam jacket 82 of the chamber.

The material exiting the tube 66 is deposited within the rotating body 96, where it is transported downwardly along the cylinder by the helical cylinder flight 122. This material is fluffed and tumbled by contact with the plates 124 as the cylinder 96 is rotated by drive motor 118. The steam within the tube 66 exits through the orifices 94 into the cylinder 96 where it continues to heat and sterilized the waste material. Residence time within the body 96 of the vessel 82 can be varied by adjusting the rotational speed of the body, and/or by periodically reversing the rotation of the body. Similarly, the feed rate of material through the extrusion tubes 66, 154 can be varied to effect a desired throughput rate by adjusting the rotational speed of the inlet and outlet screws 28, 146, and/or by periodically reversing rotation of one or both of those screws. In the case of medical waste, the material is preheated within the inlet tube 66 and retained within the cylinder 96 sufficiently to heat it to a sterilization temperature, and the rotation of the cylinder is sufficient to retain the material therein sufficiently to effect the necessary retention time to sterilize the material. In the case of MSW and paper material, including paper pulp, the temperature and retention times are adjusted such that they are sufficient to "cook" or break down such material.

When the material has been transported to the downstream end 128 of the body 96, it has been treated sufficiently either to sterilize it or to break it down, as required. The material is then emptied from the cylinder 96 and deposited into the pressurized hopper 70, where it falls downwardly into the exit screw 146. That screw 146 acts in a fashion similar to screw 28 in that it displaces the now-treated material sidewardly into the exit extrusion tube 154 where it is again compressed into a plug. As before, the plug within tube 154 is sufficiently compacted to form an airtight seal. Consequently, with the embodiment of FIGS. 1 and 3, the sterilization environment of the invention, which is accomplished by tube 66 and cylinder 96, is sealed by plugs formed within the tube 66 and the exit extrusion tube 154. Again, the seal between the rotating cylinder 96 and stationary tube 66 and stationary pressurized hopper 70 is accomplished by the rotating seals which have been described earlier and are located between those components.

As shown in FIG. 10, the compacted material is compressed into the outlet extrusion tube 154 and ultimately is deposited into the rotating drum 164 where it is tumbled and separated when it contacts the spiral ribs 176 of that drum. Moisture which is given off by the cooling material is removed through conduit 162 (and conduit 166) through a condenser 158 and is, if desired, recycled. The now-treated (sterilized, if desired), dried and broken-apart material then leaves the drum 164 where it is guided by open hopper 190 onto conveyor 200 for loading into a container and removal from the site.

As will be described below, variations can be made to the system described thus far without departing from the scope of the invention. For example, the input component 12 can be modified as shown in FIGS. 6 and 7 as 12'. The input component 12' includes an input conveyor 18' which is enclosed in a hood 42 and opens into a hopper 22 which includes a reciprocating ram 58 (see FIG. 1). That hopper 22 empties into a shredder 24 which is positioned directly above an air lock, generally designated 202. Air lock 202 includes inlet and outlet doors 204, 206 respectively, and an air lock enclosure 208. The air lock is in communication with the input injector screw 26, which is identical in construction to that shown in FIG. 3.

The operation of the input component 12' of the embodiments of FIGS. 6 and 7 is as follows. Material is placed on conveyor 18' and conveyed through hood 42 to hopper 22 where it falls downwardly into shredder 42. Feeding of the material into the shredder 42 is expedited by the reciprocating ram 58. The shredded material is permitted to exit the shredder when the inlet door 204 of air lock 202 is opened, so that shredded material collects within enclosure 208. When enclosure 208 is at or near capacity, door 204 closes and door 206 opens to allow material to fall downwardly into the feed screw enclosure 26. From there, the material is displaced sidewardly into the inlet extrusion tube 66 (see FIG. 3) and processed as described above. In another embodiment of invention shown in FIGS. 8 and 9, the treatment component 14' is modified such that the cylinder 96' terminates in a stationary door 210 which is supported on a pivotal hinge 212. The door is sealed with respect to the exit extension 126' of the body 96' by a rotatable seal. With this embodiment, the system operates on a batch mode, such that a plug of material is formed in the injection tube 66 (see FIG. 4), the material is deposited into the body 96', where it is treated and transported in a downstream direction by flight 122, and upon the completion of the sterilization process, the door 210 is opened so that the treated material can exit the body 96', where it is guided by an open hopper 214 to a removal conveyor 200.

In another embodiment, shown in FIG. 11, the cylinder 68 includes an extension 216 which is supported by bearings 218, 220 that engage raised external ribs 222, 224, respectively. The extension 216 communicates with a pressurized hopper 226 by a rotating seal 228. The hopper 226 communicates with an exit air lock 230, having an inlet door 232 and exit 234 and an air lock chamber 236. The air lock 230 deposits material onto an open hopper 240 which guides the material to the conveyor 200 for removal. Material entering the pressurized hopper 226 is allowed to fall downwardly into the air lock chamber 236 when door 232 is opened. Door 232 is then closed when the chamber 236 is at or near capacity, and door 234 is opened, to allow material to fall downwardly into the hopper 240.

Again, the embodiment shown in FIG. 11 can be used with the present invention to operate in a batch mode, at least insofar as the flow of material into pressurized hopper 226 is concerned. If the cycling of the air lock 230 is timed properly, the overall system can operate substantially continuously.

With all of the foregoing embodiments, the advantage of the system of the present invention is that a "dynamic" plug of ground material is created at at least the inlet end of a treatment chamber which, in the case of the preferred embodiment, consists of the injection tube and rotating cylinder body.

While the methods and forms of apparatus herein described constitute preferred embodiments of the invention, it is to be understood that the invention is not limited to these precise methods and forms, and that variations therein may be made without departing from the scope of the invention.

What is claimed is:

1. A system for treating material comprising:
   a pressure chamber;
   an inlet tube communicating with said pressure chamber, said inlet tube having an inner wall that tapers outwardly in a direction toward said pressure chamber;
   an inlet compression screw having a tapered shaft, said compression screw sized and positioned to feed and compress material into said inlet tube to form a plug of material therein of sufficient density to form a pressure seal for said pressure chamber; and
   an enclosure housing said compression screw, said enclosure generally conforming to said compression screw.

2. The system of claim 1 wherein said inlet tube includes inner and outer walls defining a sleeve for receiving steam.

3. The system of claim 2 wherein said inner wall of said inlet tube includes a heated, interior surface such that material passing therethrough is heated by said surface.

4. The system of claim 3 wherein said inlet tube extends into an interior of said pressure chamber.

5. The system of claim 4 wherein said inlet tube includes an end face having a plurality of perforations positioned to allow steam from said sleeve to enter and heat an interior of said sterilization chamber.

6. The system of claim 1 further comprising:
   an outlet air lock connected to an outlet opening of said pressure chamber.

7. The system of claim 6 wherein said outlet air lock includes an outlet tube communicating with said pressure chamber; and an outlet screw positioned to receive material from said pressure chamber and feed and compress said material into said outlet tube to form a plug of material therein of sufficient density to form a pressure seal for said pressure chamber.

8. The system of claim 6 wherein said outlet air lock includes an outlet hopper positioned to receive material from said pressure chamber; an inlet door positioned adjacent to said outlet hopper; an air lock chamber; and an outlet airlock door positioned on an opposite end of said pressure chamber from said inlet air lock door.

9. The system of claim 6 further comprising a drying component including an exhaust fan connected to an interior thereof to evacuate moisture-laden air therefrom, said drying component being positioned to receive material from said air lock.

10. The system of claim 9 wherein said drying component includes a rotatable cylinder having an interior wall; and at least one helical, radially-inwardly extending rib.

11. The system of claim 10 wherein said drying component rotatable cylinder includes an annular chamber interconnecting said exhaust fan with said interior of said drying component rotatable cylinder.

12. The system of claim 11 further comprising an outlet hopper positioned to receive material from said chamber and convey said material to said outlet screw.

13. The system of claim 12 further comprising a rotatable seal positioned between said outlet hopper and said pressure chamber.

14. The system of claim 13 further comprising:
   a rotatable vessel enclosing and defining said pressure chamber; and
   a motor for rotating said vessel.

15. The system of claim 14 wherein said rotatable seal interconnects said rotatable vessel and said outlet hopper.

16. The system of claim 15 wherein said rotatable seal includes a labyrinth seal.

17. The system of claim 1 further comprising:
   a rotatable vessel enclosing and defining said pressure chamber; and
   a motor for rotating said vessel.

18. The system of claim 17 further comprising a rotatable seal between said inlet tube and said rotatable vessel.

19. The system of claim 18 wherein said rotatable seal includes a labyrinth seal.

20. The system of claim 1 further comprising a drying component including an exhaust fan connected to an interior thereof to evacuate moisture-laden air therefrom, said drying component being positioned to receive material from said pressure chamber.

21. The system of claim 20 wherein said drying component includes a rotatable cylinder having an interior wall; and at least one helical, radially-inwardly extending rib.

22. A system for sterilizing waste material comprising:
a rotatable vessel enclosing and defining a sterilization chamber and
a motor for rotating said vessel;
an inlet tube extending into an interior of said sterilization chamber, said inlet tube including inner and outer walls defining a sleeve for receiving steam, said inner wall tapering outwardly in a direction toward said sterilization chamber and having an interior surface heated to a temperature sufficient to sterilize material passing therethrough, and including an end face having a plurality of perforations positioned to allow steam from said sleeve to enter and heat an interior of said sterilization chamber;
an inlet screw positioned to feed and compress material into said inlet tube to form a plug of material therein of sufficient density to form a pressure seal for said chamber;
an outlet air lock connected to an outlet opening of said sterilization chamber, said outlet air lock including an outlet tube communicating with said chamber and an outlet screw positioned to receive material from said sterilization chamber and feed and compress said material into said outlet tube to form a plug of material therein of sufficient density to form a pressure seal for said chamber;
a drying component including an exhaust fan connected to an interior thereof to evacuate moisture-laden air therefrom, said drying component being positioned to receive material from said outlet air lock, and including a rotatable cylinder having an interior wall and at least one helical, radially-inwardly extending rib;
said drying component rotatable cylinder includes an annular chamber interconnecting said exhaust fan with said interior of said drying component rotatable cylinder;
an outlet hopper positioned to receive material from said chamber and convey said material to said outlet screw;
a rotatable seal positioned between said outlet hopper and said sterilization chamber, said rotatable seal including a labyrinth seal interconnecting said rotatable vessel and said outlet hopper;
a rotatable seal between said inlet tube and said rotatable vessel, said rotatable seal including a labyrinth seal.

23. A system for treating process materials comprising:
a pressure vessel;
an inlet tube communicating with said vessel, said inlet tube having an inner wall that tapers outwardly in a direction toward said pressure vessel;
an inlet compression screw having a tapered shaft, said compression screw positioned to feed and create a material plug within said inlet tube which acts as a dynamic pressure seal for said vessel; and
an enclosure housing said compression screw, said enclosure generally conforming to said compression screw.

24. The system of claim 23 wherein said inlet tube includes an interior surface heated to a temperature sufficient to sterilize at least a portion of material passing therethrough.

25. The system of claim 24 wherein an inner wall of said inlet tube includes said interior heated surface.

26. The system of claim 23 wherein said inlet tube includes inner and outer walls defining a sleeve therebetween for receiving steam.

27. The system of claim 23 wherein said inlet tube extends into an interior of said pressure vessel.

28. The system of claim 23 wherein said inlet tube includes an inner end portion having a plurality of perforations positioned at allow steam from said sleeve to enter and heat an interior of said pressure vessel.

29. The system of claim 23 further comprising an air lock connected to an inlet of said enclosure.

30. The system of claim 29 wherein said air lock includes a receiving hopper positioned to receive material; an inlet door positioned adjacent to the inlet receiving hopper; an air lock chamber; and an outlet air lock door spaced from said inlet door.

31. The system of claim 23 further comprising a shredder positioned to discharge to said inlet screw.

32. The system of claim 31 further including a feed hopper and a reciprocating ram for feeding material into said shredder.

33. The system of claim 31 further comprising an inlet air lock positioned upstream of said shredder.

34. The system of claim 33 wherein said inlet air lock includes an inlet conveyor; an inlet air lock door; an air lock chamber; and an outlet air lock door.

35. The system of claim 34 further comprising a feed hopper interconnecting said inlet air lock and said shredder.

* * * * *

UNITED STATES PATENT AND TRADEMARK OFFICE
CERTIFICATE OF CORRECTION

PATENT NO. : 6,588,690 B1
DATED : July 8, 2003
INVENTOR(S) : Koenig

It is certified that error appears in the above-identified patent and that said Letters Patent is hereby corrected as shown below:

Drawings,
Fig. 3, please delete "28" and insert -- 27 --.
Fig. 3, please delete "30" and insert -- 31 --.

Signed and Sealed this

Nineteenth Day of October, 2004

JON W. DUDAS
*Director of the United States Patent and Trademark Office*